United States Patent [19]
Samuel et al.

[11] 3,952,415
[45] Apr. 27, 1976

[54] J-SHAPED PIN FOR MAKING DENTAL PROTHESIS

[76] Inventors: Robert A. Samuel, 3603 Ethan Court, San Jose, Calif. 95123; Michael W. Layne, 112 Capistrano Drive, Los Gatos, Calif. 95030

[22] Filed: Feb. 18, 1975

[21] Appl. No.: 550,370

[52] U.S. Cl. .................................................. 32/11
[51] Int. Cl.² ........................................... A61C 13/00
[58] Field of Search ............. 32/11, 70, 71, 6, 10 R, 32/13, 10 A; 85/49, 13

[56] References Cited
UNITED STATES PATENTS

| | | | |
|---|---|---|---|
| 401,343 | 4/1889 | Gildemeyer | 85/49 |
| 1,110,091 | 9/1914 | White | 85/49 |
| 1,639,530 | 8/1927 | Payson | 85/49 |
| 2,067,359 | 1/1937 | Tumminello | 85/49 |
| 2,314,481 | 3/1943 | Grooks | 85/49 X |
| 2,323,362 | 7/1943 | Weiss | 85/49 |
| 2,533,062 | 12/1950 | Spink | 85/49 |
| 3,704,519 | 12/1972 | Lystager | 32/11 |

Primary Examiner—Louis G. Mancene
Assistant Examiner—Jack Q. Lever
Attorney, Agent, or Firm—Jack M. Wiseman

[57] ABSTRACT

In the making of fixed dental prothesis, a model is employed, which is an accurate replica of the patient's teeth and gums. For reinforcement, the model is fixed to a base. A model comprises a replica of the teeth remaining in the patient's mouth and a replica of teeth to be prepared by restorative dentistry. For preparing the teeth by restorative dental techniques, a die is used. It is desired that the die be removed from and replaced in the model with facility, be indexed accurately relative to the model, and have stability while positioned in the model against forces applied in the practice of prothesis, and also be removable from the base on which the model is secured. Toward this end, a pin is fixed in the die having a locating leg and an indexing leg interconnected by an arcuate portion of the pin. The legs extend outwardly from the die to be received by the base to which the model is secured. The locating leg and the indexing leg have conical or wedgelike configurations and the base has openings to receive the legs contoured to conform to the configuration of the legs.

23 Claims, 7 Drawing Figures

U.S. Patent   April 27, 1976   3,952,415
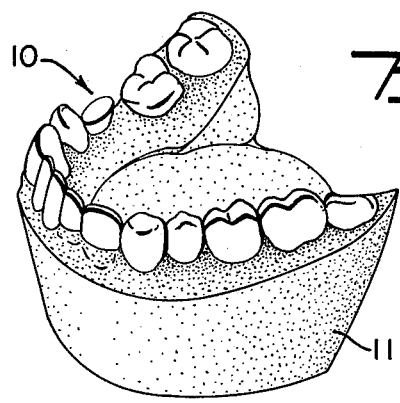
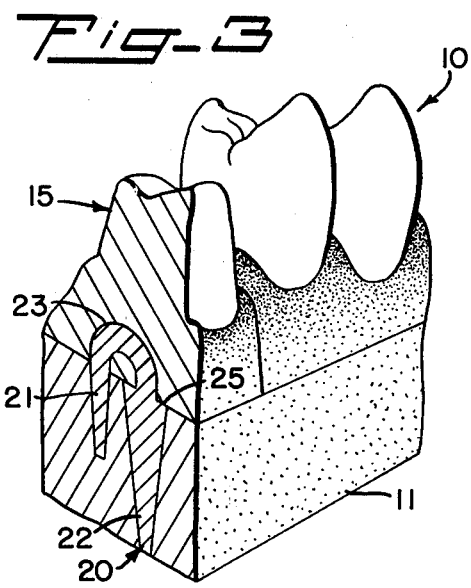
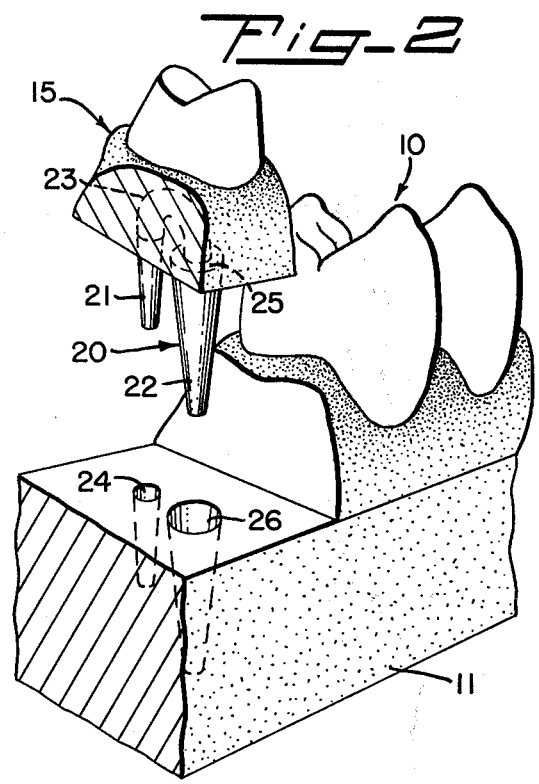
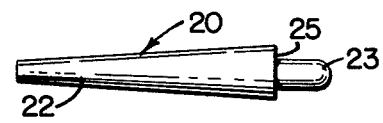
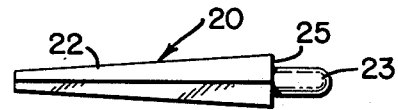
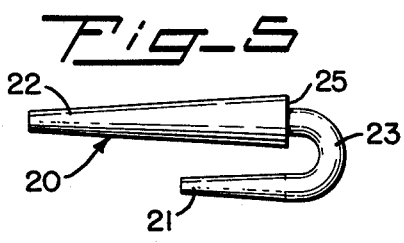
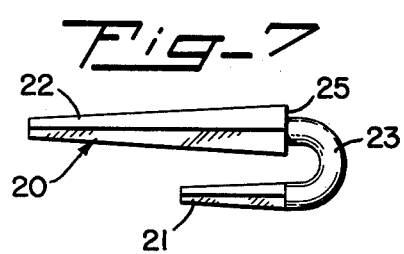

J-SHAPED PIN FOR MAKING DENTAL PROTHESIS

BACKGROUND OF THE INVENTION

The present invention relates in general to models employed in restorative or prothetic dentistry, and more particularly to an indexing and locating pin fixed in a removable die of a model and received by a base to which the model is secured.

In the making of a fixed dental prothesis (i.e. gold and ceramic crown or bridge) requires that an accurate replica of the existing teeth and gums (dentition) be made. The replicas, herein referred to as models, are made by taking an impression of dentition. Material capable of adapting to the exact shape and dimension of the dentition are, for example, silicon rubber and agar hydrocolloid. The impression is a "negative" model in which plaster, such as calcium sulfatehemihydrate, is poured. Upon removal from the impression, the plaster forms the model on which the prothesis is constructed. The model is secured to a base of plaster to increase its overall strength.

The plaster model comprises teeth which are replicas of the teeth remaining in the mouth of the patient and a replica of the teeth to be prepared by prothetic or restorative dentistry. It is the teeth prepared for the prothesis to be developed upon that employs an indexing and locating pin.

The replica of the teeth to be prepared by prothetic or restorative dentistry is known as a die. It is desired in restorative dentistry that the die be removable from and replaceable in the model. Further, the die should be indexed in the model to reposition itself in all planes after removal. The replaced die should not vary or move from its original position in the model in any plane more than ±0.001 inch. Also the die in its vertical removal movement from the model should be free to move in all planes immediately upon the vertical removal action to provide free-play for removal of undercut or eccentric dies. The removal is in a direction perpendicular to the occular plane. Of course, the removal is from the base upon which the model is secured. While disposed in the model, the die should be retained in place as to be unyielding to the normal forces and pressures, for example torsion, that may be applied to it during the fabrication of the prothesis. Thus, a die must be capable of being indexed in the model, must be removable with facility and must be stable against forces applied thereto during the fabrication of the prothesis.

Heretofore, dowel pins have been employed for indexing a removable die of a model. Such dowel pins have generally been made of brass. The dowel pins were fixed in the die and extended therefrom to be received by a suitable opening in the base. The dowel pins serve to index and locate the die relative to the model. Typically, the dowel pin had a cylindrical configuration or a surface equi-distance from the axis of the pin. At times, a portion of the cylindrical surface would have a flat taper portion extending in the axial direction equi-distance from the axis thereof.

Customarily, the dowel pin had a knurled end for retention in the die. In some instances, adhesive, such as cyano acrylate ester, on a smooth surface was employed to secure the dowel pin in the die. At other times, the dowel pin had a flared or flanged end for retention in the die.

Additionally, the dies heretofore employed had two separate and independent dowel pins extending from the die. Some dowel pins used plastic sleeves around the indexing portion of the pin for greater accuracy in indexing and locating the die in the model. The sleeve additionally may have facilitated the removal of the die from the model.

In the patent to Weissman, U.S. Pat. No. 3,153,283, there is shown a dowel pin with a complementary dowel sleeve, which are cast from metal. The dowel pin has a tapered shank at the lower portion thereof. The sleeve afforded indexing for the pin removable therefrom and insertable therein. Additionally, the sleeve facilitated the insertion and removal of the pin.

An Accu-Twin pin sold by Unitek Corporation of Monrovia, California, employed an indexing leg and a locating leg joined by a rectilinear portion. However, the surfaces of the legs are equi-distance from the axis of the legs, respectively, such as one would find in a cylindrical surface, or flat surfaces parallel to the longitudinal center line. A Pin-Dex pin manufactured by Whaldent, employed two separate and independent pins as above mentioned.

In the patent to Stengle, U.S. Pat. No. 3,478,428, a row of parallel, conically shaped guide pins were fixed to a retaining base in apparatus to facilitate the production of cast dental models. The pins serve as guide members for the die for indexing the same in the model. At least one pin in imbedded in each die. One surface of each pin is flattened to prevent rotational movement of the die.

The patent to Waltke U.S. Pat. No. 3,453,736 discloses dowel pins of tubular and conical shapes. Additionally, a dowel with the lower end thereof conical and the upper end thereof flared is also shown therein.

Other patents of interest are:
U.S. Pat. No. 2,705,837
U.S. Pat. No. 2,655,724
U.S. Pat. No. 1,867,300
U.S. Pat. No. 1,780,117

The pins heretofore employed in prothetic or restorative dentistry for removably mounting the die in the model exhibited poor indexing. The pins using flat surfaces had a tendency to wear the index surfaces into the plaster. The dies are subject to high torsional forces during the fabrication of the prothesis and thus the wearing of the index surfaces caused position and rotational error. The pins using knurls, flanges, or flares tend to be easily loosened from the die to result in poor retention. This occurs because of shallow insertion into the die or because of soft plaster used in the fabrication of the die. Pins using adhesive tend to be unreliable because of poor adhesion caused by moisture retained in the plaster.

Tapered pins with one or more flat surfaces parallel to the longitudinal center line of the pin restrict movement in the direction adjacent to the flat surface. Cylindrical pins are limited in movement to a direction perpendicular to the occlusal plane.

SUMMARY OF THE INVENTION

An indexing and locating pin for a die removably mounted in a model in prothetic or restorative dentistry in which the pin includes a locating leg and an indexing leg interconnected by a portion of the pin and in which each leg has a configuration in which the wall thereof gradually decreases in cross-sectional area in the direction the leg is received by openings in a base on which the model is secured.

By virtue of the indexing and locating pin having legs with a conical or wedgelike configuration, the pin enables the die to be released from the base with facility and minimum restriction. The employment of a unitary pin with a locating leg and an indexing leg permits the indexing action and the locating action to be performed simultaneously. Thus, there is provided simultaneous, accurate indexing with instant play, mobility and release. The release is a 360° rather than a 270° release.

The portion of the pin interconnecting the indexing leg and the locating leg has improved the retention of the pin in the die. The retention surface of the pin in the die is not only increased, but the configuration thereof lends itself to improved seating stability. The retention portion of the pin strengthens the die by acting as an internal stress member in the die.

Additionally, the locating leg and the indexing leg provide positioning of the die in the model. Torsional forces are reduced in the indexing surface through the relatively large movement between the indexing leg and the locating leg. This reduces rotational movement of the die relative to the model while the prothesis is being fabricated. Thus, the pin enables the operator to fabricate prothesis with greater and more consistent accuracy, while minimizing time and effort expended on inaccurate prothesis because of misaligned or broken dental dies.

DESCRIPTION OF THE DRAWING

FIG. 1 is a perspective view of a model used in prothetic or restorative dentistry secured to a base.

FIG. 2 is a fragmentary perspective view of the model shown in FIG. 1 with a die thereof removed from the model.

FIG. 3 is a fragmentary perspective view of the model shown in FIG. 1 to illustrate the pin of the present invention retaining the die in the model and with the pin received by the base on which the model is secured.

FIG. 4 is a side elevation view of the pin embodying the present invention with conical legs.

FIG. 5 is a front elevation view of the pin shown in FIG. 4.

FIG. 6 is a side elevation view of a modification of the pin embodying the present invention with wedge-shaped legs.

FIG. 7 is a front elevation of the pin shown in FIG. 6.

DESCRIPTION OF THE PREFERRED EMBODIMENTS

In prothetic or restorative dentistry, a fixed dental prothesis is fabricated, which may be a gold or ceramic crown or bridge. This procedure requires an accurate replica of the existing teeth and gums. The existing teeth and gums are called dentition and the replica is called a model. Initially, an impression is made of the dentitions. Material commonly employed for taking the impression is silicon rubber or agar hydrocolloid. The impression is a "negative" model in which plaster is poured. Commonly employed plaster for this purpose is a calcium sulfatehemihydrate. Upon removal from the impression, the plaster forms a model on which the prothesis is constructed.

Illustrated in FIG. 1 is a model 10, which is secured to a base 11 for improved overall strength. The base 11 is generally made of the same material as is the model 10 and the model 10 is fixed to the base 11 in a well-known manner by adhesion. The plaster model 10 comprises replica of teeth remaining in the patient's mouth and a replica of teeth to be prepared by restorative or prothetic dentistry.

It is the replica of teeth from which a prothetic restoration is prepared that embodies the present invention. The portion of the model 10 from which the prothesis is to be developed on or fabricated from is a die 15 (FIGS. 3 and 4). The die 15 is generally found of the same material as is the model, namely: a plaster of calcium sulfatehemihydrate.

In order to use the die 15 for prothetic restoration, the die 15 must be removable from the model 10 and must be replaced in the model 10 (FIG. 2) and must be replaced in the model 10 (FIG. 3) so as not to vary more than ±0.001 inch from its original position in any plane. As previously described, an impression of the patient's mouth is first made in the usual manner. Thereafter, the model 10 is cast from the impression and when a slurry of plaster material has been fully poured, a pin 20 is inserted into the plaster adjacent to the tooth recess or cavity before the plaster material has fully hardened or cured. The pin is inserted so that its orientation is generally perpendicular to the plane of occlusion.

After the plaster has fully hardened with the pin 20 therein, a separator medium, such as "Vasoline", is placed on the lower wall of the die 15. Thereupon, additional plaster material is poured thereover up to a predetermined level to form the base 11. At this time, the base 11 and model 10 are fully hardened and cured. To remove the die 15 from the model 10, the model 10 is cut by a saw or the like along the sides of the die 15. The lower wall of the die 15 is separable through the separator medium. The pin 20 is preferably made of a suitable metal, such as alloy 360 brass. The legs of the pin 20 are received by the openings formed in the base 11, while the base 11 was formed.

According to the present invention, the pin 20 (FIGS. 4 and 5) comprises an indexing leg 21 and locating leg 22. Interconnecting the legs 21 and 22 to form an integral or unitary structure is an arcuate retention portion 23. It is the retention portion 23 that is embedded in the die 15 for improved retention of the pin 20 in the die 15. At the junction of the locating leg 22 and the retention portion 23 is a reduced diameter shoulder 25. Along the shoulder 25 is disposed the bottom wall of the die 15. The legs 21 and 22 along with the retention portion 23 form an inverted J-shape.

The legs 21 and 22 of the pin 20 are contoured so that the legs 21 and 22, respectively, gradually decrease in cross-sectional area taken in the direction along the longitudinal axis thereof and toward the base. More specifically, the legs 21 and 22 of the pin 20 may have a conical configuration (FIGS. 4 and 5) or the legs 21 and 22 of the pin 20 may have a wedge shape (FIGS. 6 and 7). The gradual reduction of the cross-sectional area of the respective legs 21 and 22 exist along the entire periphery or circumference of the walls thereof.

The legs 21 and 22 of the pin 20 are received respectively by openings 24 and 26 of the base 11. The contours of the openings 24 and 26 conform to the configuration of the legs 21 and 22, respectively. Thus, the die 15 can be removed from the model 10 and replaced in the model 10 by reinserting the legs 21 and 22 into the openings 24 and 26 of the base 11.

From the foregoing, it is to be observed that the gradually reduced cross-sectional areas of the respective legs 21 and 22 of the pin 20 are present through the circumference or perimeter of the wall thereof, thus providing a full, instantaneous release of the die from the base 11 upon vertical movement. Additionally, the indexing leg 21 and the locating leg 22 are received simultaneously in the openings 24 and 26, respectively, of the base 11. Hence, the locating action and the indexing action are performed concurrently. By having the retention portion 23 for the pin 20, the retention surface of the pin 20 is increased to improve the ability of the die 15 to stably hold the pin 20. Further, the die 15 is strengthened by the ability of the retention portion 23 to absorb stress applied to the legs 21 and 22. In addition to the legs 21 and 22 providing positive positioning for the pin 20, torsional forces on the leg 21 are reduced by the movement represented by the length of the retention portion 23 as the distance between the legs 21 and 22. Thus, rotational movement of the die 15 relative to the model 10 is reduced while the prothesis is being fabricated.

We claim:
1. An assembly for prothetic dentistry comprising:
   a. a base, said base being formed with a plurality of openings;
   b. a model secured to said base;
   c. a die in said model removably attached to said base; and
   d. a pin fixed in said die, said pin comprising:
      1. a locating leg projecting from said die and received by one of said openings in said base, said locating leg having a wall with a configuration in which the cross-sectional area of the wall gradually and uniformly decreases;
      2. an indexing leg projecting from said die and received by another of said openings in said base, said indexing leg having a wall with a configuration in which the cross-sectional area of indexing leg wall gradually and uniformly decreases; and
      3. a retention portion interconnecting said locating leg and said indexing leg and embodied in said die.

2. An assembly as claimed in claim 1 wherein said one opening has a configuration conforming to the contour of the wall of said locating leg and said other opening has a configuration conforming to the contour of the wall of said indexing leg.

3. An assembly as claimed in claim 2 wherein said locating leg has a conical configuration.

4. An assembly as claimed in claim 2 wherein said indexing leg has a conical configuration.

5. An assembly as claimed in claim 2 wherein said locating leg has a wedge configuration.

6. An assembly as claimed in claim 2 wherein said indexing leg has a wedge configuration.

7. An assembly as claimed in claim 3 wherein said indexing leg has a conical configuration.

8. An assembly as claimed in claim 5 wherein said indexing leg has a wedge configuration.

9. An assembly as claimed in claim 7 wherein said retention portion has an arcuate configuration.

10. An assembly as claimed in claim 8 wherein said retention portion has an arcuate configuration.

11. An assembly as claimed in claim 9 wherein said indexing leg is shorter than said locating leg, whereby said pin has an inverted J-shape.

12. An assembly as claimed in claim 10 wherein said indexing leg is shorter than said locating leg, whereby said pin has an inverted J-shape.

13. A pin for removably positioning a die in a model in prothetic dentistry comprising:
   a. a locating leg, said locating leg having a wall with a configuration in which the cross-sectional area of the wall gradually and uniformly decreases, said locating leg terminating at its distal end with a blunt surface;
   b. an indexing leg, said indexing leg having a wall with a configuration in which the cross-sectional area of the indexing leg wall gradually and uniformly decreases, said indexing leg terminating at its distal end with a blunt surface; and
   c. a retention portion interconnecting said indexing leg and said locating leg at the proximal ends thereof.

14. A pin as claimed in claim 13 wherein said locating leg has a conical configuration.

15. A pin as claimed in claim 13 wherein said indexing leg has a conical configuration.

16. A pin as claimed in claim 13 wherein said locating leg has a wedge configuration.

17. A pin as claimed in claim 13 wherein said indexing leg has a wedge configuration.

18. A pin as claimed in claim 14 wherein said indexing leg has a conical configuration.

19. A pin as claimed in claim 18 wherein said retention portion has an arcuate configuration.

20. A pin as claimed in claim 16 wherein said indexing leg has a wedge configuration.

21. A pin as claimed in claim 20 wherein said retention portion has an arcuate configuration.

22. A pin as claimed in claim 19 wherein said indexing leg is shorter than said locating leg, whereby said pin has an inverted J-shape.

23. A pin as claimed in claim 21 wherein said indexing leg is shorter than said locating leg, whereby said pin has an inverted J-shape.

* * * * *